US00PP36242P2

(12) United States Plant Patent
Boxriker

(10) Patent No.: US PP36,242 P2
(45) Date of Patent: Nov. 5, 2024

(54) ***OSTEOSPERMUM* PLANT NAMED 'KLEOE22627'**

(50) Latin Name: ***Osteospermum ecklonis* Norl.**
Varietal Denomination: KLEOE22627

(71) Applicant: KLEMM + SOHN GMBH & CO. KG, Stuttgart (DE)

(72) Inventor: Maike Boxriker, Stuttgart (DE)

(73) Assignee: KLEMM + SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 18/220,266

(22) Filed: Jul. 11, 2023

(51) Int. Cl.
*A01H 5/02* (2018.01)
*A01H 6/14* (2018.01)

(52) U.S. Cl.
USPC ..... Plt./360
CPC ..... *A01H 6/148* (2018.05)

(58) Field of Classification Search
USPC ..... Plt./360
CPC ..... A01H 5/02
See application file for complete search history.

(56) References Cited

PUBLICATIONS https://www.dickmanfarms.com/assets/Planner-2024.pdf; Oct. 20, 2023; 2 pages.*
https://www.bfgsupply.com/media/8263/2024-millstadt-product-program.pdf; Oct. 20, 2023; 2 pages.*
https://www.ballseed.com/PlantInfo/?phid=046105136051873; Oct. 20, 2023; 1 page.*

* cited by examiner

*Primary Examiner* — Kent L Bell
(74) *Attorney, Agent, or Firm* — Weatherly IP Solutions, LLC; James M. Weatherly

(57) ABSTRACT

A new Osteospermum plant particularly distinguished by plants having good branching and light pink ray florets with yellow tips, is disclosed.

1 Drawing Sheet

Genus and species: *Osteospermum ecklonis* Norl.
Variety denomination: 'KLEOE22627'.

BACKGROUND OF THE NEW PLANT

The present invention comprises a new and distinct variety of Osteospermum, botanically known as *Osteospermum ecklonis* Norl., and hereinafter referred to by the variety name 'KLEOE22627'. 'KLEOE22627' originated from a cross-pollination conducted in Summer through Autumn 2017 in Nairobi, Kenya between the proprietary female Osteospermum variety 'OE-2011-0238' (unpatented) and the proprietary male Osteospermum variety 'OE-2016-3217' (unpatented).

The seeds from the cross were collected and in winter of 2018 sown in Stuttgart, Germany and plants were grown for evaluation. An individual plant designated 'KLEOE22627' was selected in May of 2018 in Stuttgart, Germany. In 2018 'KLEOE22627' was first vegetatively propagated by vegetative terminal cuttings in Stuttgart, Germany. 'KLEOE22627' was found to reproduce true to type in successive generations of asexual propagation via vegetative terminal cuttings.

SUMMARY

The following are the most outstanding and distinguishing characteristics of this new variety when grown under normal horticultural practices in Stuttgart, Germany.

1. Good branching; and
2. Light pink ray florets with yellow tips.

DESCRIPTION OF THE PHOTOGRAPH

This new Osteospermum plant is illustrated by the accompanying photograph which shows a close-up the foliage, buds, and mature inflorescence. The photograph is of a 11-week-old plant outdoors in Stuttgart, Germany in June 2022. The colors shown are as true as can be reasonably obtained by conventional photographic procedures.

DESCRIPTION OF THE NEW VARIETY

The following detailed descriptions set forth the distinctive characteristics of 'KLEOE22627'. The data which define these characteristics were collected in Stuttgart Germany in May 2023 on plants that were potted in week 8. Color references are to The R.H.S. Colour Chart of The Royal Horticultural Society of London (R.H.S.), 5$^{th}$ edition (2007).

Classification:
*Family*.—Asteraceae.
*Botanical*.—*Osteospermum ecklonis* Norl.
*Common*.—Osteospermum.
*Designation*.—'KLEOE22627'.

Parentage:
*Female parent*.—The proprietary female Osteospermum variety 'OE-2011-0238' (unpatented).
*Male parent*.—The proprietary male Osteospermum variety 'OE-2016-3217' (unpatented).

Plant:

*Form and habit*.—Herbaceous perennial but usually cultivated as an annual; not frost resistant.

*Growth habit*.—Upright.

*Branching habit*.—Normal.

*Height* (*from top of soil, including inflorescence*).—15.0 cm.

*Width* (*including inflorescences*).—24.0 cm.

*Propagation*.—Vegetative cuttings.

*Time to produce a finished flowering plant*.—10 to 17 weeks.

*Time to initiate and develop roots*.—4 weeks.

*Root description*.—Fine, white RHS 155C.

Stems:

*Total number of branches per plant* (*calculated at the base of the plant*).—5.

*Length*.—13.0 cm.

*Diameter*.—0.4 cm.

*Internode length*.—1.0 cm.

*Color*.—RHS 144A.

*Texture*.—Smooth.

*Anthocyanin*.—Absent.

Leaves:

*Arrangement*.—Alternate.

*Shape*.—Obovate.

*Apex*.—Acute.

*Base*.—Acute.

*Margin*.—Serrate.

*Immature color*.—Upper surface: RHS 137C. Lower surface: RHS 146B.

*Mature color*.—Upper surface: RHS 137B. Lower surface: RHS 138A.

*Length*.—3.2 cm.

*Width*.—1.3 cm.

*Texture and appearance*.—Upper surface: Leathery. Lower surface: Leathery with fine hairs.

*Petioles*.—Absent.

*Venation pattern*.—Pinnate.

*Venation color*.—Upper surface: RHS 144A. Lower surface: RHS 144A.

Flower buds:

*Shape*.—Round.

*Length*.—0.8 cm.

*Diameter*.—1.0 cm.

*Color* (*at tight bud just before the ray florets unfold*).—RHS 145B.

Inflorescence:

*Type*.—Composite, single.

*Blooming habit*.—Upright with longer flower stems.

*Quantity of inflorescences per plant*.—17.

*Lastingness of the inflorescences on the plant*.—10 to 15 days.

*Fragrance*.—Slightly present; fresh.

*Inflorescence diameter*.—5.3 cm.

*Inflorescence depth*.—0.6 cm.

*Disc diameter*.—1.0 cm.

Disc floret:

*Quantity per inflorescence*.—About 70.

*Shape*.—Tubular.

*Tube color*.—Closed: RHS 158C. Mature: RHS NN155A.

*Length*.—0.5 cm.

*Diameter* (*at apex*).—0.1 cm.

*Apex*.—Acute.

*Apex color*.—RHS 94A.

*Base*.—Acute.

*Base color*.—RHS NN155C.

*Margin*.—Entire.

*Texture*.—Smooth.

Ray floret:

*Quantity per inflorescence*.—19.

*Shape*.—Oblanceolate.

*Color*.—Upper surface (Color changes during the maturation of the inflorescences, colors below are the colors at the time of evaluation): Mature inflorescences: RHS 70B with RHS 14B tips. Young inflorescences: RHS 65A and RHS 14B tips. Lower surface: RHS 14B with RHS N77B stripes.

*Length*.—2.6 cm.

*Width*.—0.7 cm.

*Apex*.—Obtuse.

*Base*.—Acute.

*Margin*.—Entire.

*Texture* (*upper and lower surfaces*).—Smooth.

*Peduncle*.—Length: 4.5 cm. Diameter: 0.2 cm. Texture: Smooth with hairs. Color: RHS 144A.

Phyllaries:

*Texture*.—Smooth with fine hairs.

*Arrangement*.—Single.

*Observed quantity per plant*.—18.

*Shape*.—Lanceolate.

*Color*.—Upper surface: RHS 144A. Lower surface: RHS 144B.

*Length*.—1.0 cm.

*Width*.—0.2 cm.

*Apex*.—Acute.

*Base*.—Obtuse.

*Margin*.—Entire.

*Texture*.—Upper surface: Smooth with fine hairs. Lower surface: Smooth.

Reproductive organs:

*Androecium location*.—On the disc floret.

*Stamens*.—Quantity: Numerous, 50-100. Shape: Filamentous. Filament length: 0.5 cm. Filament diameter: Less than 0.1 cm. Anther: Shape: Lanceolate. Color: RHS 79A. Length: 0.1 cm. Diameter: Less than 0.1 cm. Pollen: Color: RHS 21A. Amount: Abundant.

*Gynoecium location*.—On the base of the ray florets and disc florets.

*Pistils*.—Number: Numerous, 50-100. Length: 0.2 cm. Diameter: Less than 0.1 cm.

*Stigma*.—Color: RHS N77A. Shape: Filamentous. Length: 0.2 cm. Diameter: Less than 0.1 cm.

*Style*.—Color: RHS N77A. Length: 0.1 cm. Diameter: Less than 0.1 cm.

Fruit and seed set: None observed.

Disease and pest/insect resistance: No disease and pest/insect resistance observed.

COMPARISON WITH PARENTAL LINES AND KNOWN VARIETY

'KLEOE22627' is a distinct variety of Osteospermum and is distinguished from its parents as described in Table 1.

TABLE 1

| Comparison with Parental Lines | | | |
|---|---|---|---|
| Characteristic | 'KLEOE22627' | Female Parent | Male Parent |
| Ray Floret Color | Light pink with yellow tips | Pink | Pink with light center |

'KLEOE22627' is most similar to the commercial Osteospermum variety 'KLEOE19396' (U.S. Plant Pat. No. 31,026). Differences between the varieties are described in Table 2.

TABLE 2

| Comparison with Similar Variety | | |
|---|---|---|
| Characteristic | 'KLEOE22627' | 'KLEOE19396' (U.S. Plant Pat. No. 31,026) |
| Ray Floret color | Light pink with yellow tips | Orange with purple center |
| Branching | Good | Medium |
| Earliness | Very early | Flowers later than the variety of the application |

I claim:

1. A new and distinct cultivar of Osteospermum Plant Named 'KLEOE22627' as described and illustrated herein.

* * * * *

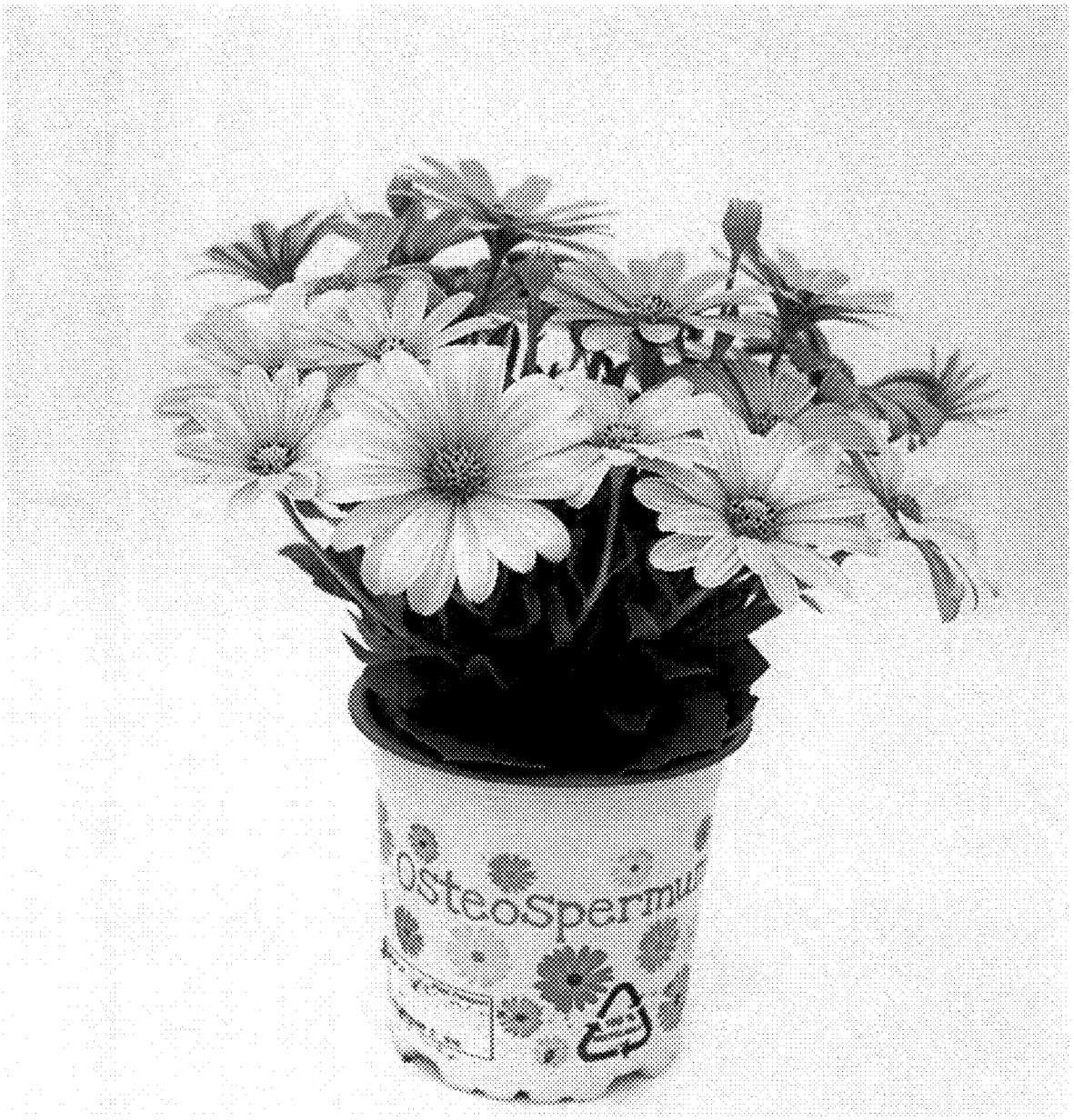
OsteoSperm